United States Patent
Govari et al.

(10) Patent No.: US 8,990,039 B2
(45) Date of Patent: Mar. 24, 2015

(54) CALIBRATION SYSTEM FOR A PRESSURE-SENSITIVE CATHETER

(71) Applicant: Biosense Webster (Israel) Ltd., New Brunswick, NJ (US)

(72) Inventors: Assaf Govari, Haifa (IL); Yaron Ephrath, Karkur (IL); Andres Claudio Altmann, Haifa (IL)

(73) Assignee: Biosense Webster (Israel) Ltd. (IL)

( * ) Notice: Subject to any disclaimer, the term of this patent is extended or adjusted under 35 U.S.C. 154(b) by 5 days.

(21) Appl. No.: 13/975,778

(22) Filed: Aug. 26, 2013

(65) Prior Publication Data

US 2014/0032152 A1    Jan. 30, 2014

Related U.S. Application Data

(63) Continuation of application No. 12/646,242, filed on Dec. 23, 2009, now Pat. No. 8,521,462.

(51) Int. Cl.
| | |
|---|---|
| *G01L 27/00* | (2006.01) |
| *A61B 5/1495* | (2006.01) |
| *A61B 5/00* | (2006.01) |
| *G01D 5/244* | (2006.01) |

(52) U.S. Cl.
CPC .......... *G01D 5/24452* (2013.01); *A61B 5/1495* (2013.01); *A61B 2560/0223* (2013.01); *A61B 5/6885* (2013.01)
USPC .......................................................... 702/98

(58) Field of Classification Search
USPC ......... 702/85, 98, 104, 41–44, 150, 152, 153; 600/463, 407, 424
See application file for complete search history.

(56) References Cited

U.S. PATENT DOCUMENTS

| | | | |
|---|---|---|---|
| 3,841,150 A | 10/1974 | Pearson | |
| 3,971,364 A | 7/1976 | Fletcher et al. | |
| 4,764,114 A | 8/1988 | Jeffcoat et al. | |
| 4,856,993 A | 8/1989 | Maness et al. | |
| 4,930,494 A | 6/1990 | Takehana et al. | |

(Continued)

FOREIGN PATENT DOCUMENTS

| | | |
|---|---|---|
| DE | 19750441 A | 6/1999 |
| EP | 928601 A1 | 7/1999 |

(Continued)

OTHER PUBLICATIONS

Instron Marketing Brochure, "Medical Device Testing Systems", Instron 2007 http://web.archive.org/web/20080318092822/http://www.instron.com.tr/wa/library/streamfile.aspx?doc=1678&downland=true.

(Continued)

*Primary Examiner* — Manuel L Barbee

(57) ABSTRACT

A calibration apparatus includes a fixture, which is coupled to accept a probe so that a distal tip of the probe presses against a point in the fixture and produces first measurements indicative of a deformation of the distal tip relative to a distal end of the probe, in response to pressure exerted on the distal tip. A sensing device is coupled to the fixture and is configured to produce second measurements of a mechanical force exerted by the distal tip against the point. A calibration processor is configured to receive the first measurements from the probe, to receive the second measurements from the sensing device and to compute, based on the first and second measurements, one or more calibration coefficients for assessing the pressure as a function of the first measurements.

12 Claims, 5 Drawing Sheets

(56) References Cited

U.S. PATENT DOCUMENTS

| | | |
|---|---|---|
| 5,263,493 A | 11/1993 | Avitall |
| 5,368,564 A | 11/1994 | Savage |
| 5,391,199 A | 2/1995 | Ben Haim |
| 5,462,527 A | 10/1995 | Stevens-Wright et al. |
| 5,487,757 A | 1/1996 | Truckai et al. |
| 5,499,542 A | 3/1996 | Morlan |
| 5,542,434 A | 8/1996 | Imran et al. |
| 5,558,091 A | 9/1996 | Acker et al. |
| 5,563,354 A | 10/1996 | Kropp |
| 5,662,124 A | 9/1997 | Wilk |
| 5,673,695 A | 10/1997 | McGee et al. |
| 5,680,860 A | 10/1997 | Imran |
| 5,685,878 A | 11/1997 | Falwell et al. |
| 5,728,149 A | 3/1998 | Laske et al. |
| 5,769,843 A | 6/1998 | Abela et al. |
| 5,826,576 A | 10/1998 | West |
| 5,833,608 A | 11/1998 | Acker |
| 5,836,894 A | 11/1998 | Sarvazyan |
| 5,860,974 A | 1/1999 | Abele |
| 5,861,024 A | 1/1999 | Rashidi |
| 5,902,248 A | 5/1999 | Millar et al. |
| 5,916,147 A | 6/1999 | Boury |
| 5,944,022 A | 8/1999 | Nardella et al. |
| 5,947,320 A | 9/1999 | Bordner et al. |
| 5,964,757 A | 10/1999 | Ponzi |
| 5,974,320 A | 10/1999 | Ward et al. |
| 5,983,126 A | 11/1999 | Wittkampf |
| 6,048,329 A | 4/2000 | Thompson et al. |
| 6,063,022 A | 5/2000 | Ben Haim |
| 6,123,699 A | 9/2000 | Webster, Jr. |
| 6,171,277 B1 | 1/2001 | Ponzi |
| 6,177,792 B1 | 1/2001 | Govari et al. |
| 6,183,463 B1 | 2/2001 | Webster, Jr. |
| 6,198,974 B1 | 3/2001 | Webster, Jr. |
| 6,201,387 B1 | 3/2001 | Govari |
| 6,203,493 B1 | 3/2001 | Ben Haim |
| 6,216,027 B1 | 4/2001 | Willis et al. |
| 6,226,542 B1 | 5/2001 | Reisfeld |
| 6,239,724 B1 | 5/2001 | Doron et al. |
| 6,241,724 B1 | 6/2001 | Fleischman et al. |
| 6,266,551 B1 | 7/2001 | Osadchy et al. |
| 6,272,371 B1 | 8/2001 | Shlomo |
| 6,272,672 B1 | 8/2001 | Conway |
| 6,301,496 B1 | 10/2001 | Reisfeld |
| 6,332,089 B1 | 12/2001 | Acker et al. |
| 6,334,837 B1 | 1/2002 | Hein |
| 6,335,617 B1 | 1/2002 | Osadchy et al. |
| 6,351,549 B1 | 2/2002 | Souluer |
| 6,436,059 B1 | 8/2002 | Zanelli |
| 6,456,864 B1 | 9/2002 | Swanson et al. |
| 6,484,118 B1 | 11/2002 | Govari |
| 6,551,302 B1 | 4/2003 | Rosinko et al. |
| 6,569,098 B2 | 5/2003 | Kawchuk |
| 6,574,492 B1 | 6/2003 | Ben-Haim et al. |
| 6,584,856 B1 | 7/2003 | Biter et al. |
| 6,602,242 B1 | 8/2003 | Fung et al. |
| 6,612,992 B1 | 9/2003 | Hossack et al. |
| 6,618,612 B1 | 9/2003 | Acker et al. |
| 6,690,963 B2 | 2/2004 | Ben Haim et al. |
| 6,695,808 B2 | 2/2004 | Tom |
| 6,711,429 B1 | 3/2004 | Gilboa et al. |
| 6,727,371 B2 | 4/2004 | Müller et al. |
| 6,814,733 B2 | 11/2004 | Schwartz et al. |
| 6,835,173 B2 | 12/2004 | Couvillon, Jr. |
| 6,892,091 B1 | 5/2005 | Ben Haim et al. |
| 6,915,149 B2 | 7/2005 | Ben Haim |
| 6,945,956 B2 | 9/2005 | Waldhauser et al. |
| 6,964,205 B2 | 11/2005 | Papakostas et al. |
| 6,973,339 B2 | 12/2005 | Govari |
| 6,997,924 B2 | 2/2006 | Schwartz et al. |
| 7,077,823 B2 | 7/2006 | McDaniel |
| 7,156,816 B2 | 1/2007 | Schwartz et al. |
| 7,235,070 B2 | 6/2007 | Vanney |
| 7,297,116 B2 | 11/2007 | Varghese et al. |
| 7,306,593 B2 | 12/2007 | Keidar et al. |
| 7,306,599 B2 | 12/2007 | Karasawa et al. |
| 7,311,704 B2 | 12/2007 | Paul et al. |
| 7,397,364 B2 | 7/2008 | Govari |
| 7,435,232 B2 | 10/2008 | Liebschner |
| 7,465,288 B2 | 12/2008 | Dudney et al. |
| 7,481,774 B2 | 1/2009 | Brockway et al. |
| 7,536,218 B2 | 5/2009 | Govari et al. |
| 7,604,605 B2 | 10/2009 | Zvuloni |
| 7,662,151 B2 | 2/2010 | Crompton, Jr. et al. |
| 7,681,432 B2 | 3/2010 | Hay et al. |
| 7,686,767 B2 | 3/2010 | Maschke |
| 7,914,440 B2 | 3/2011 | Otawara |
| 7,959,601 B2 | 6/2011 | McDaniel et al. |
| 7,984,659 B2 | 7/2011 | Fujimoto et al. |
| 8,043,216 B2 | 10/2011 | Matsumura |
| 8,046,049 B2 | 10/2011 | Govari et al. |
| 8,083,691 B2 | 12/2011 | Goldenberg et al. |
| 8,137,275 B2 | 3/2012 | Fan et al. |
| 8,374,819 B2 | 2/2013 | Govari et al. |
| 8,521,462 B2 * | 8/2013 | Govari et al. ............... 702/104 |
| 2001/0047129 A1 | 11/2001 | Hall et al. |
| 2001/0047133 A1 | 11/2001 | Gilboa et al. |
| 2002/0002329 A1 | 1/2002 | Avitall |
| 2002/0065455 A1 | 5/2002 | Ben Haim et al. |
| 2002/0068866 A1 | 6/2002 | Zikorus et al. |
| 2002/0068931 A1 | 6/2002 | Wong et al. |
| 2002/0165461 A1 | 11/2002 | Hayzelden et al. |
| 2002/0193781 A1 | 12/2002 | Loeb |
| 2003/0120150 A1 | 6/2003 | Govari |
| 2003/0120195 A1 | 6/2003 | Milo et al. |
| 2003/0130615 A1 | 7/2003 | Tom |
| 2003/0158494 A1 | 8/2003 | Dahl et al. |
| 2003/0187389 A1 | 10/2003 | Morency et al. |
| 2004/0049255 A1 | 3/2004 | Jain et al. |
| 2004/0064024 A1 | 4/2004 | Sommer |
| 2004/0068178 A1 | 4/2004 | Govari |
| 2004/0097806 A1 | 5/2004 | Hunter et al. |
| 2004/0102769 A1 | 5/2004 | Schwartz et al. |
| 2004/0147920 A1 | 7/2004 | Keidar |
| 2004/0244464 A1 | 12/2004 | Hajdukiewicz et al. |
| 2004/0254458 A1 | 12/2004 | Govari |
| 2005/0033135 A1 | 2/2005 | Govari |
| 2005/0080429 A1 | 4/2005 | Freyman et al. |
| 2005/0096590 A1 | 5/2005 | Gullickson et al. |
| 2005/0228274 A1 | 10/2005 | Boese et al. |
| 2005/0277875 A1 | 12/2005 | Selkee |
| 2006/0009690 A1 | 1/2006 | Fuimaono et al. |
| 2006/0009735 A1 | 1/2006 | Viswanathan et al. |
| 2006/0015096 A1 | 1/2006 | Hauck et al. |
| 2006/0064038 A1 | 3/2006 | Omata et al. |
| 2006/0074297 A1 | 4/2006 | Viswanathan |
| 2006/0173480 A1 | 8/2006 | Zhang |
| 2006/0184106 A1 | 8/2006 | McDaniel et al. |
| 2006/0200049 A1 | 9/2006 | Leo et al. |
| 2006/0247618 A1 | 11/2006 | Kaplan et al. |
| 2007/0060832 A1 | 3/2007 | Levin |
| 2007/0060847 A1 | 3/2007 | Leo et al. |
| 2007/0100332 A1 | 5/2007 | Paul et al. |
| 2007/0106114 A1 | 5/2007 | Sugimoto et al. |
| 2007/0142749 A1 | 6/2007 | Khatib et al. |
| 2007/0151391 A1 | 7/2007 | Larkin et al. |
| 2007/0156114 A1 | 7/2007 | Worley et al. |
| 2007/0161882 A1 | 7/2007 | Pappone |
| 2007/0167740 A1 | 7/2007 | Grunewald et al. |
| 2007/0167818 A1 | 7/2007 | Osborn et al. |
| 2007/0179492 A1 | 8/2007 | Pappone |
| 2007/0185397 A1 | 8/2007 | Govari et al. |
| 2007/0191829 A1 | 8/2007 | McGee et al. |
| 2007/0197927 A1 | 8/2007 | Ofek et al. |
| 2007/0197939 A1 | 8/2007 | Wallace et al. |
| 2007/0282211 A1 | 12/2007 | Ofek et al. |
| 2008/0009750 A1 | 1/2008 | Aeby et al. |
| 2008/0015568 A1 | 1/2008 | Paul et al. |
| 2008/0051704 A1 | 2/2008 | Patel et al. |
| 2008/0065111 A1 | 3/2008 | Blumenkranz et al. |
| 2008/0071267 A1 | 3/2008 | Wang et al. |
| 2008/0077049 A1 | 3/2008 | Hirshman |
| 2008/0146918 A1 | 6/2008 | Magnin et al. |
| 2008/0183075 A1 | 7/2008 | Govari et al. |

(56) References Cited

U.S. PATENT DOCUMENTS

| | | |
|---|---|---|
| 2008/0200843 A1 | 8/2008 | Williams et al. |
| 2008/0249467 A1 | 10/2008 | Burnett et al. |
| 2008/0249522 A1 | 10/2008 | Pappone et al. |
| 2008/0255540 A1 | 10/2008 | Selkee |
| 2008/0269606 A1 | 10/2008 | Matsumura |
| 2008/0275428 A1 | 11/2008 | Tegg et al. |
| 2008/0275442 A1 | 11/2008 | Paul et al. |
| 2008/0275465 A1 | 11/2008 | Paul et al. |
| 2008/0281319 A1 | 11/2008 | Paul et al. |
| 2008/0287777 A1 | 11/2008 | Li et al. |
| 2008/0288038 A1 | 11/2008 | Paul et al. |
| 2008/0294144 A1 | 11/2008 | Leo et al. |
| 2008/0294158 A1 | 11/2008 | Pappone et al. |
| 2009/0010021 A1 | 1/2009 | Smith et al. |
| 2009/0093806 A1 | 4/2009 | Govari et al. |
| 2009/0138007 A1 | 5/2009 | Govari et al. |
| 2009/0158511 A1 | 6/2009 | Maze et al. |
| 2009/0177111 A1 | 7/2009 | Miller et al. |
| 2009/0275966 A1 | 11/2009 | Mitusina |
| 2009/0287118 A1 | 11/2009 | Malek |
| 2009/0294361 A1 | 12/2009 | Larsen |
| 2009/0306515 A1 | 12/2009 | Matsumura |
| 2009/0306650 A1 | 12/2009 | Govari et al. |
| 2010/0063478 A1 | 3/2010 | Selkee |
| 2010/0069921 A1 | 3/2010 | Miller et al. |
| 2010/0121138 A1 | 5/2010 | Goldenberg et al. |
| 2010/0137845 A1 | 6/2010 | Ramstein et al. |
| 2010/0152574 A1 | 6/2010 | Erdman et al. |
| 2010/0160770 A1 | 6/2010 | Govari et al. |
| 2010/0160778 A1 | 6/2010 | Eskandari et al. |
| 2010/0168620 A1 | 7/2010 | Klimovitch et al. |
| 2010/0168918 A1 | 7/2010 | Zhao et al. |
| 2010/0292566 A1 | 11/2010 | Nagano et al. |
| 2010/0298826 A1 | 11/2010 | Leo et al. |
| 2011/0054354 A1 | 3/2011 | Hunter et al. |
| 2011/0054355 A1 | 3/2011 | Hunter et al. |
| 2011/0071436 A1 | 3/2011 | Althoefer et al. |
| 2011/0130648 A1 | 6/2011 | Beeckler et al. |
| 2011/0153252 A1 | 6/2011 | Govari et al. |
| 2011/0153253 A1 | 6/2011 | Govari et al. |
| 2011/0160556 A1 | 6/2011 | Govari |
| 2011/0172538 A1 | 7/2011 | Sumi |
| 2011/0184406 A1 | 7/2011 | Selkee |
| 2011/0307207 A1 | 12/2011 | Govari et al. |
| 2012/0004576 A1 | 1/2012 | Govari et al. |
| 2012/0041295 A1 | 2/2012 | Schultz |
| 2012/0089358 A1 | 4/2012 | Ludwin et al. |
| 2012/0108988 A1 | 5/2012 | Ludwin et al. |
| 2012/0149966 A1 | 6/2012 | Ludwin et al. |
| 2012/0149967 A1 | 6/2012 | Ludwin et al. |
| 2012/0150075 A1 | 6/2012 | Ludwin et al. |
| 2012/0184864 A1 | 7/2012 | Harlev et al. |
| 2012/0184865 A1 | 7/2012 | Harlev et al. |
| 2012/0253167 A1 | 10/2012 | Bonyak et al. |
| 2012/0259194 A1 | 10/2012 | Selkee |
| 2012/0271145 A1 | 10/2012 | Govari et al. |
| 2012/0310116 A1 | 12/2012 | Ludwin et al. |
| 2012/0316407 A1 | 12/2012 | Anthony et al. |
| 2013/0018306 A1 | 1/2013 | Ludwin |

FOREIGN PATENT DOCUMENTS

| | | |
|---|---|---|
| EP | 980693 A1 | 2/2000 |
| EP | 1502555 A1 | 2/2005 |
| EP | 1586281 A1 | 10/2005 |
| EP | 1690564 A1 | 8/2006 |
| EP | 1743575 A2 | 1/2007 |
| EP | 1820464 A1 | 8/2007 |
| EP | 1897581 A2 | 3/2008 |
| EP | 2000789 A2 | 12/2008 |
| EP | 2047797 A2 | 4/2009 |
| EP | 2127604 A1 | 12/2009 |
| EP | 2130508 B1 | 12/2009 |
| EP | 2196143 A1 | 6/2010 |
| EP | 2305115 A1 | 4/2011 |
| EP | 2338412 A1 | 6/2011 |
| EP | 2172240 B1 | 12/2012 |
| EP | 2338411 B1 | 11/2013 |
| JP | 8243168 A | 9/1996 |
| JP | 2000126301 A | 5/2000 |
| JP | 2000508224 A | 7/2000 |
| JP | 2005040215 | 2/2005 |
| JP | 2005237964 A | 9/2005 |
| JP | 2005345215 A | 12/2005 |
| JP | 2006064465 A | 3/2006 |
| JP | 2006255401 A | 9/2006 |
| JP | 2007181696 A | 7/2007 |
| WO | 95/10326 A | 4/1995 |
| WO | WO 96/05768 A | 2/1996 |
| WO | 97/29709 A | 8/1997 |
| WO | 97/29710 A | 8/1997 |
| WO | WO 97/29678 A | 8/1997 |
| WO | 98/29032 A | 7/1998 |
| WO | 03/020139 A | 3/2003 |
| WO | 2006/029563 A | 3/2006 |
| WO | 2006/086152 A | 8/2006 |
| WO | 2006/092563 A | 9/2006 |
| WO | 2006/135483 A2 | 12/2006 |
| WO | 2007/015139 A2 | 2/2007 |
| WO | 2007/025230 A | 3/2007 |
| WO | 2007/050960 A | 5/2007 |
| WO | 2007/067938 A | 6/2007 |
| WO | 2007/076312 A2 | 7/2007 |
| WO | 2007/082216 A | 7/2007 |
| WO | WO 2007/098494 A1 | 8/2007 |
| WO | 2007/111182 A | 10/2007 |
| WO | 2008/053402 A1 | 5/2008 |
| WO | 2008/147599 A1 | 12/2008 |
| WO | 2009/065140 A1 | 5/2009 |
| WO | 2009/078280 A | 6/2009 |
| WO | 2009/085470 A | 7/2009 |
| WO | 2010/008975 A | 1/2010 |
| WO | 2011/046874 A1 | 4/2011 |

OTHER PUBLICATIONS

Instron, "Series 3300 Load Frames, References Manual Equipment", Instron, pp. 1-5 and 1-10, 2004.

Peirs, J. et. al., "Design of an Optical Force Sensor for Force Feedback during Minimally Invasive Robotic Surgery", Eurosensors XVII, 2003, pp. 1063-1066, http://mech.kuleuven.be/micro/pub/medic/Paper_Eurosensors_2003_MIS_senorextended.pdf.

European Search Report mailed on Mar. 28, 2011 from corresponding European Patent Application No. 10252191.1.

European Search Report mailed on Sep. 23, 2011 from related European Patent Application No. 11169251.3.

Biter, William J. et al., "Magnetic Wire Strain Sensor", 33rd International Sampe Technical Conference, Nov. 5-8, 2001, vol. 33, pp. 12-23, Seattle, WA.

Biter, William J. et al., "Magnetic Wire for Monitoring Strain in Composites", *Sensors*, Jun. 2001, www.sensormag.com, pp. 110-114.

Guo, Shuxiang et al., "Control and Experimental results of a Catheter Operating System", Feb. 21-26, 2009, Proceedings of the 2008 IEEE, International Conference on Robotics and Biomimetics, Bankok, Thailand, pp. 91-95.

Kanagaratnam, Prapa et. al., "Experience of robotic catheter ablation in humans using novel remotely steerable catheter sheath", Journal of Interventional Cardiac Electrophysiology. vol. 21, No. 1, p. 19-26 (2008).

Okumura, M.D. Yasuo et al. "A Systematic Analysis of In Vivo Contact Forces on Virtual Catheter Tip/Tissue Surface Contact during Cardiac Mapping and Intervention", Journal of Cardiovascular Electrophysiology, Jun. 2008, pp. 632-640, vol. 19, No. 6.

Partial European Search Report mailed on Sep. 18, 2009 from related European Patent Application No. 08253265.6.

Partial European Search Report mailed on Dec. 7, 2009 from related European Patent Application No. 09251502.2.

European Search Report mailed on Mar. 8, 2010 from related European Patent Application No. 09252143.4.

(56) References Cited

OTHER PUBLICATIONS

Partial European Search Report mailed on Mar. 29, 2010 from related European Patent Application No. 09252879.3.
European Search Report mailed on Mar. 2, 2011 from related European Patent Application No. 10175931.4.
European Search Report mailed on Mar. 28, 2011 from related European Patent Application No. 10252189.5.
European Search Report mailed on Mar. 30, 2011 from related European Patent Application No. 10252020.2.
European Search Report mailed on May 16, 2011 from related European Patent Application No. 10252232.3.
European Search Report mailed on Aug. 5, 2011 from related European Patent Application No. 11158804.2.
European Search Report mailed on Sep. 20, 2011 from related European Patent Application No. 11250066.5.
European Search Report mailed on Oct. 28, 2011 from related European Patent Application No. 11171842.5.
European Search Report mailed on Nov. 17, 2011 from related European Patent Application No. 11177600.1.
European Search Report mailed on Feb. 15, 2012 from related European Patent Application No. 11182854.7.
European Search Report mailed on May 2, 2012 from related European Patent Application No. 11189326.9.
European Search Report mailed on Jun. 4, 2012 from related European Patent Application No. 12163784.7.
European Search Report mailed on Nov. 20, 2012 from related European Patent Application No. 12176163.9.
European Search Report mailed on Feb. 11, 2013 from related European Patent Application No. 11187525.8.
European Search Report mailed on Apr. 9, 2013 from related European Patent Application No. 13150145.4.

* cited by examiner

CALIBRATION SYSTEM FOR A PRESSURE-SENSITIVE CATHETER

CROSS REFERENCE TO RELATED APPLICATION

This application is a continuation U.S. patent application Ser. No. 12/646,242, filed Dec. 23, 2009, now issued as U.S. Pat. No. 8,521,462, which is assigned to the assignee of the present patent application and whose disclosure is incorporated herein by reference.

FIELD OF THE INVENTION

The present invention relates generally to invasive probes, and specifically to calibrating pressure sensors in invasive probes.

BACKGROUND

A wide range of medical procedures involve placing objects, such as sensors, tubes, catheters, dispensing devices and implants, within the body. Position sensing systems have been developed for tracking such objects. Magnetic position sensing is one of the methods known in the art. In magnetic position sensing, magnetic field generators are typically placed at known positions external to the patient. A magnetic field sensor within the distal end of a probe generates electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

When placing a probe within the body, it may be desirable to have the distal tip of the probe in direct contact with body tissue. The contact can be verified, for example, by measuring the contact pressure between the distal tip and the body tissue. U.S. Patent Application Publications 2007/0100332 and 2009/0093806, whose disclosures are incorporated herein by reference, describe methods of sensing contact pressure between the distal tip of a catheter and tissue in a body cavity using a force sensor embedded in the catheter. The distal tip of the catheter is coupled to the distal end of the catheter insertion tube by a resilient member, such as a spring, which deforms in response to force exerted on the distal tip when it presses against endocardial tissue. A magnetic position sensor within the catheter senses the deflection (location and orientation) of the distal tip relative to the distal end of the insertion tube. Movement of the distal tip relative to the insertion tube is indicative of deformation of the resilient member, and thus gives an indication of the pressure.

SUMMARY OF THE INVENTION

An embodiment of the present invention provides a calibration apparatus including a fixture, a sensing device and a calibration processor. The fixture is coupled to accept a probe so that a distal tip of the probe presses against a point in the fixture and produces first measurements indicative of a deformation of the distal tip relative to a distal end of the probe, in response to pressure exerted on the distal tip. The sensing device is coupled to the fixture and is configured to produce second measurements of a mechanical force exerted by the distal tip against the point. The calibration processor is configured to receive the first measurements from the probe, to receive the second measurements from the sensing device and to compute, based on the first and second measurements, one or more calibration coefficients for assessing the pressure as a function of the first measurements.

In some embodiments, the fixture is coupled to cause the probe to press against the point at one or more predefined angles, and the calibration processor is configured to compute the calibration coefficients as a function of the predefined angles. The apparatus may include a dome covering the fixture, the dome having a plurality of insertion holes that are configured to direct the probe to the point at the predefined angles. Alternatively, the apparatus may include a receptacle configured to hold the distal end, a track coupled to the receptacle and configured to position the receptacle at multiple angles relative to the point, and a lift configured to raise the fixture so as to cause the distal tip to press against the point. The apparatus may include an input device coupled to the calibration processor and configured to accept the predefined angles.

In another embodiment, the fixture includes a cone-shaped cup. In yet another embodiment, the fixture holds the probe in a temperature-controlled liquid. In still another embodiment, the sensing device includes a load cell. In an embodiment, the calibration processor is configured to store the calibration coefficients in a memory that is coupled to the probe. The memory may include an Electronically Erasable Programmable Read Only Memory ($E^2$PROM).

There is also provided, in accordance with an embodiment of the present invention, a method of calibrating, including inserting a probe having a distal tip into a fixture, pressing the distal tip against a point in the fixture so as to cause a deformation of the distal tip relative to a distal end of the probe in response to pressure exerted on the distal tip, receiving from the probe first measurements indicative of the deformation, receiving from a sensing device coupled to the fixture second measurements indicative of a mechanical force exerted by the distal tip against the point, and computing, based on the first and second measurements, one or more calibration coefficients for assessing the pressure as a function of the first measurements.

BRIEF DESCRIPTION OF THE DRAWINGS

The disclosure is herein described, by way of example only, with reference to the accompanying drawings, wherein.

DETAILED DESCRIPTION OF EMBODIMENTS

Some invasive probes comprise pressure sensors for measuring the contact pressure between the probe and intra-body tissue. For example, the distal tip of a cardiac catheter may comprise a pressure sensor, which deforms in response to the pressure exerted by the distal tip on the endocardial tissue. A position sensor in the catheter measures the deflection of the distal tip, and thus provides an indication of the contact pressure. In many practical cases, however, the relationship between the actual contact pressure and the reading of the position sensor varies from one catheter to another.

In order to ensure accurate pressure measurements, embodiments of the present invention provide methods and systems for calibrating probes (e.g., catheters) fitted with pressure sensors. In some embodiments, a calibration apparatus comprises a fixture for accepting a catheter at a certain angle, and a sensing device (e.g., a load cell) for measuring the mechanical force exerted by the catheter against a given point in the fixture. When the catheter is inserted into the fixture at a given angle and pressed against the given point, the catheter produces deformation (e.g., deflection) measurements of its distal tip, and the sensing device produces force measurements.

In some embodiments, a calibration processor receives the deflection measurements from the catheter and the force measurements from the sensing device, and computes calibration coefficients for assessing the pressure exerted by the catheter as a function of the deflection measurements.

In some embodiments, the calibration is performed for different engagement angles between the catheter and the point in the fixture. In some embodiments, the calibration coefficients are stored in a non-volatile memory that is coupled to the catheter. When the catheter is later used in a medical system, the actual pressure exerted by the catheter's distal tip on the body tissue can be derived with high accuracy from the deflection measurements, using the calibration coefficients.

Figure 1:
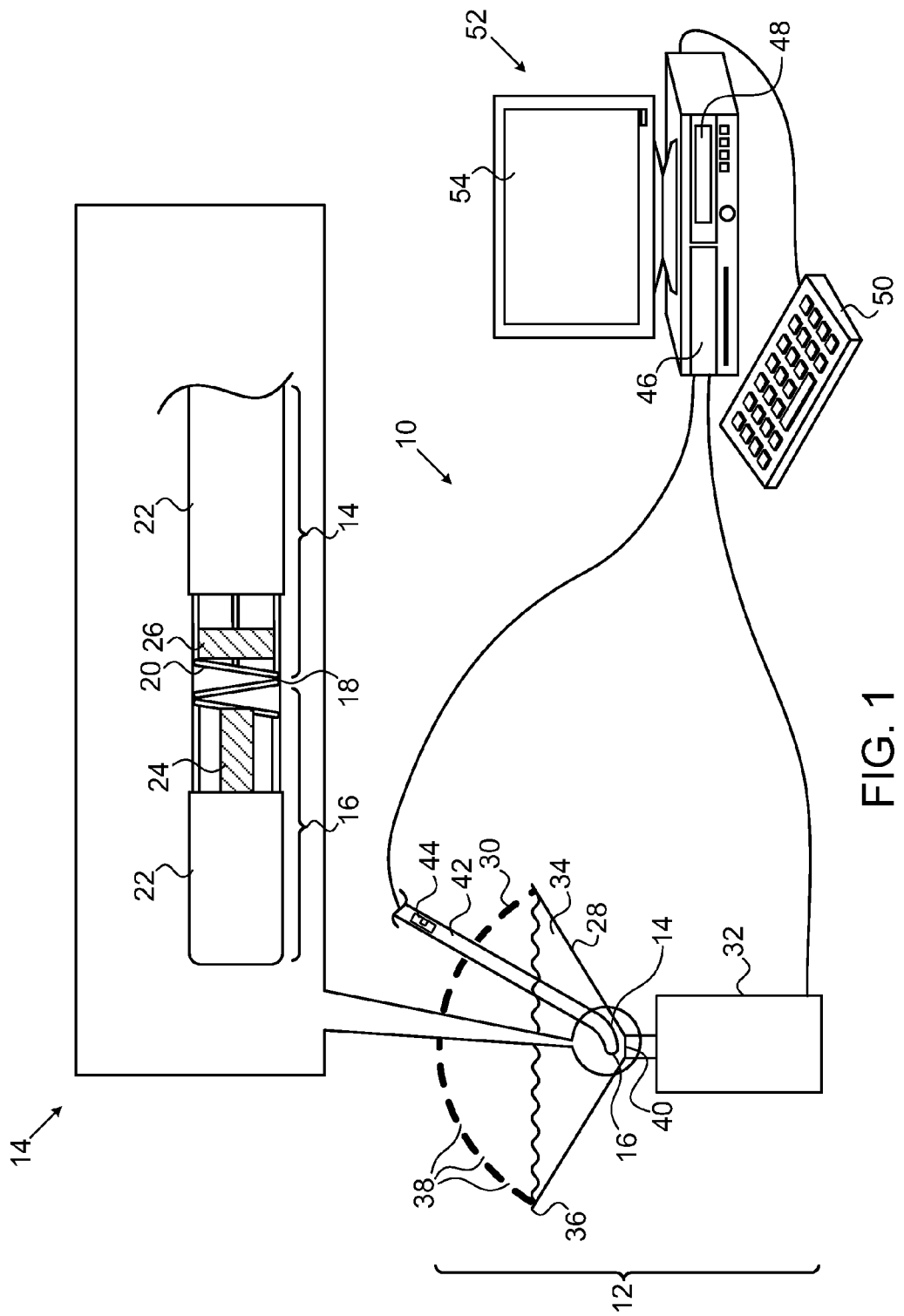
FIG. 1 is a schematic pictorial illustration of a calibration system for a pressure-sensitive catheter, in accordance with an embodiment of the present invention.

FIG. 1 is an illustration of a calibration system 10 for a pressure-sensitive catheter, in accordance with an embodiment of the present invention. System 10 comprises a calibration apparatus 12 coupled to a calibration unit 52. In the embodiment described hereinbelow, system 10 is used for calibrating a probe 42, in the present example a catheter for therapeutic and/or diagnostic purposes in a heart or in other body organs.

Probe 42 comprises a distal end 14, with a distal tip 16 connected to the distal end via a joint 18. Distal end 14 and distal tip 16 are both covered by a flexible, insulating material 22. The area of joint 18 is covered, as well, by a flexible, insulating material, which may be the same as material 22 or may be specially adapted to permit unimpeded bending and compression of the joint, (This material is cut away in FIG. 1 in order to expose the internal structure of the catheter.) Distal tip 16 is typically relatively rigid, by comparison with distal end 14.

Distal tip 16 is connected to distal end 14 by a resilient member 20. In FIG. 1, the resilient member has the form of a coil spring, but other types of resilient components may alternatively be used for this purpose. Resilient member 20 permits a limited range of relative movement between tip 16 and distal end 14 in response to forces exerted on the distal tip.

Distal tip 16 contains a magnetic position sensor 24. Sensor 24 may comprise one or more miniature coils, and typically comprises multiple coils oriented along different axes. Distal end 14 contains a miniature magnetic field generator 26 near resilient member 20. Typically, field generator 26 comprises a coil, which is driven by a current conveyed through the catheter from calibration unit 52. Alternatively, position sensor 24 may comprise either another type of magnetic sensor, an electrode which serves as a position transducer, or position transducers of other types, such as impedance-based or ultrasonic position sensors. Although FIG. 1 shows a probe with a single position sensor, embodiments of the present invention may utilize probes with more than one position sensors.

The magnetic field created by field generator 26 causes the coils in sensor 24 to generate electrical signals at the drive frequency of the field generator. The amplitudes of these signals will vary depending upon the location and orientation of distal tip 16 relative to distal end 14. A calibration processor 46 in calibration unit 52 processes these signals in order to determine the axial displacement and the magnitude of the angular deflection of the distal tip relative to distal end 14. (Because of the axial symmetry of the field generated by a coil, only the magnitude of the deflection can be detected using a single coil in field generator 26, and not the direction of the deflection. Optionally, field generator 26 may comprise two or more coils, in which case the direction of deflection may be determined, as well). The magnitudes of the displacement and deflection may be combined by vector addition to give a total magnitude of the movement of distal tip 16 relative to distal end 14.

The relative movement of distal tip 16 relative to distal end 14 gives a measure of the deformation of resilient member 20. Thus, the combination of field generator 26 with sensor 24 serves as a pressure sensing system. By virtue of the combined sensing of displacement and deflection, this pressure sensing system reads the pressure correctly regardless of whether the pressure is exerted on distal tip 16 head-on or at an angle. Further details of this sort of probe and position sensor are described in U.S. Patent Application Publications 2009/0093806 and 2009/0138007, cited above.

Probe 42 also comprises a non-volatile memory 44, such as electronically erasable programmable read only memory ($E^2$PROM), which stores calculation coefficients computed during calibration. As discussed supra, when the catheter is later used in a medical system, the actual pressure exerted by the catheter's distal tip on body tissue can be derived with high accuracy from deflection measurements, using the calibration coefficients stored in memory 44.

Calibration apparatus 12 comprises a fixture 28 that is configured to accept a probe to be calibrated. In the embodiment of FIG. 1, fixture 28 comprises a cup (e.g., a cone-shaped cup) having a top 36 and a base 40. In the present example, top 36 is wider than base 40. In alternative embodiments, fixtures having any other suitable mechanical configurations can also be used.

Fixture 28 may contain a temperature controlled liquid 34, which is held at a typical human body temperature (e.g., using a thermostat and a heating element). Using this technique, the calibration procedure of probe 42 is carried out at a temperature that closely resembles the operating temperature of the probe in the body. Temperature control may be important because the resiliency or other mechanical properties of elements of the probe may vary sharply with temperature. For example, joint 18 may contain elements such as a nickel titanium alloy (also referred to as NiTi or Nitinol) spring and a plastic outer covering (i.e., insulating material 22), whose resiliency may vary with the temperature of liquid 34.

To control the angle of engagement between catheter 42 and fixture 28, an operator (not shown) inserts the catheter into one of multiple insertion holes 38 in a dome 30 covering fixture 28. Each of the insertion holes may accept the catheter at a different angular position. The insertion holes are configured to direct distal tip 16 to press against a given point of fixture 28. In the configuration shown in FIG. 1, insertion holes 38 direct distal tip 16 to press against base 40.

In addition to fixture 28 and dome 30, calibration apparatus 12 comprises a load cell 32 coupled to base 40. The load cell measures the downward mechanical force exerted by the distal tip on base 40. Although the system shown in FIG. 1 measures the downwards force using load cell 32, system 10 may use any other suitable type of sensor to measure the downward force, and such sensors are thus considered to be within the spirit and scope of this invention.

Both load cell 32 and probe 42 are connected to calibration unit 52 via suitable interfaces (e.g., cables and connectors). Calibration unit 52 comprises calibration processor 46, a memory 48, a display 54 and an input device 50, such as a keyboard. Processor 46 typically comprises a general-purpose computer, with suitable front end and interface circuits for receiving signals from position sensor 24 and load cell 32, as well as for controlling the other components of calibration unit 52. Processor 46 may be programmed in software to carry out the functions that are described herein. The software may be downloaded to processor 46 in electronic form, over a network, for example, or it may be provided on tangible media, such as optical, magnetic or electronic memory media. Alternatively, some or all of the functions of processor 46 may be carried out by dedicated or programmable digital hardware components.

Figure 2:
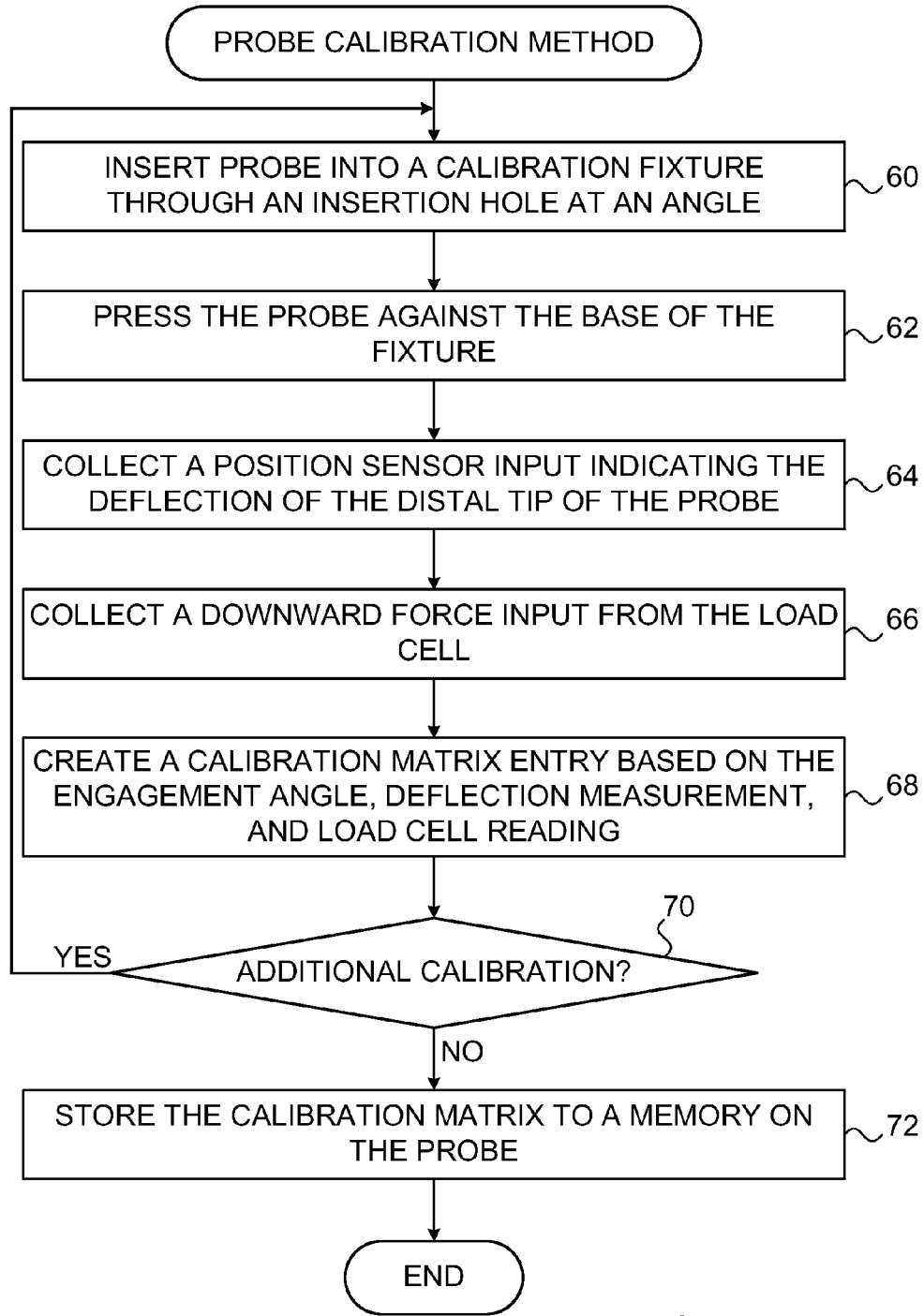
FIG. 2 is a flow diagram that schematically illustrates a method of calibrating a pressure-sensitive catheter, in accordance with an embodiment of the present invention.

FIG. 2 is a flow diagram that schematically illustrates a method of calibrating a pressure-sensitive catheter, in accordance with an embodiment of the present invention. To calibrate probe 42, the operator inserts the catheter into one of insertion holes 38 (step 60) and presses distal tip 16 against base 40 (step 62). The configuration of fixture 28 and dome 30 helps ensure that distal tip 16 will press against base (i.e., the same point of the fixture) regardless of which insertion hole is used for calibration. Typically, each insertion hole defines a different angle of engagement of the catheter with respect to base 40.

Pressing distal tip 16 against base 40 causes catheter 42 to bend at joint 18, thereby deflecting the distal tip. Position sensor 24 in distal tip 16 outputs a signal indicative of the deflection of the distal tip relative to distal end 14. Simultaneously, load cell 32 outputs a measurement indicative of the downward mechanical force exerted by distal tip 16 on base 40. Both the deflection and downward force measurements are sent to calibration unit 52, where the operator enters the engagement angle for this calibration step via keyboard 50.

In some embodiments, insertion holes 38 are labeled with respective identifiers. During the calibration process, the operator enters the identifier of the insertion hole being used into calibration unit 52 via input device 50. In an alternative embodiment, dome 30 may comprise one more proximity sensors, which automatically detect the insertion hole into which the catheter is inserted. When the operator inserts catheter 42 into one of the insertion holes, the proximity sensors will send electrical signals to calibration unit 52, and processor 46 will analyze the electrical signals to determine which of the insertion hole is being used. Any suitable type of proximity sensors, such as optical sensors or Hall-effect sensors, can be used.

Calibration unit 52 accepts the deflection measurement from sensor 24 in the probe (step 64), the downward force measurement from load cell 32 (step 66), and the angle of engagement from the operator. Based on these three inputs, processor 46 computes calibration coefficients for calibrating the deflection measurements of probe 42 (step 68). By mapping a position measurement from position sensor 24 against a force vector from load cell 32 at a given engagement angle, the calibration coefficient determines the force on distal tip 16 based on the position sensor measurements. In other words, a given calibration coefficient translates the deflection measurement of tip 16 into an actual pressure reading, for a given engagement angle.

If more calibration points are desired (step 70), then the method returns to step 60 above. Otherwise, processor 46 stores the calibration matrix to memory 44 on the probe (step 72), and the method terminates. In some embodiments, the operator may collect multiple data points for a given engagement angle (a given insertion hole 38) by exerting different amounts of pressure on the probe.

To store the calibration matrix, processor 46 may store an analytic calculation to memory 44 based on the computed coefficients. Alternatively, processor 46 may store a lookup table with inter-measurement interpolation to memory 44. In some embodiments, processor 46 may store a combination of the two (e.g., coefficients chosen according to a region) to memory 44.

Figure 3:
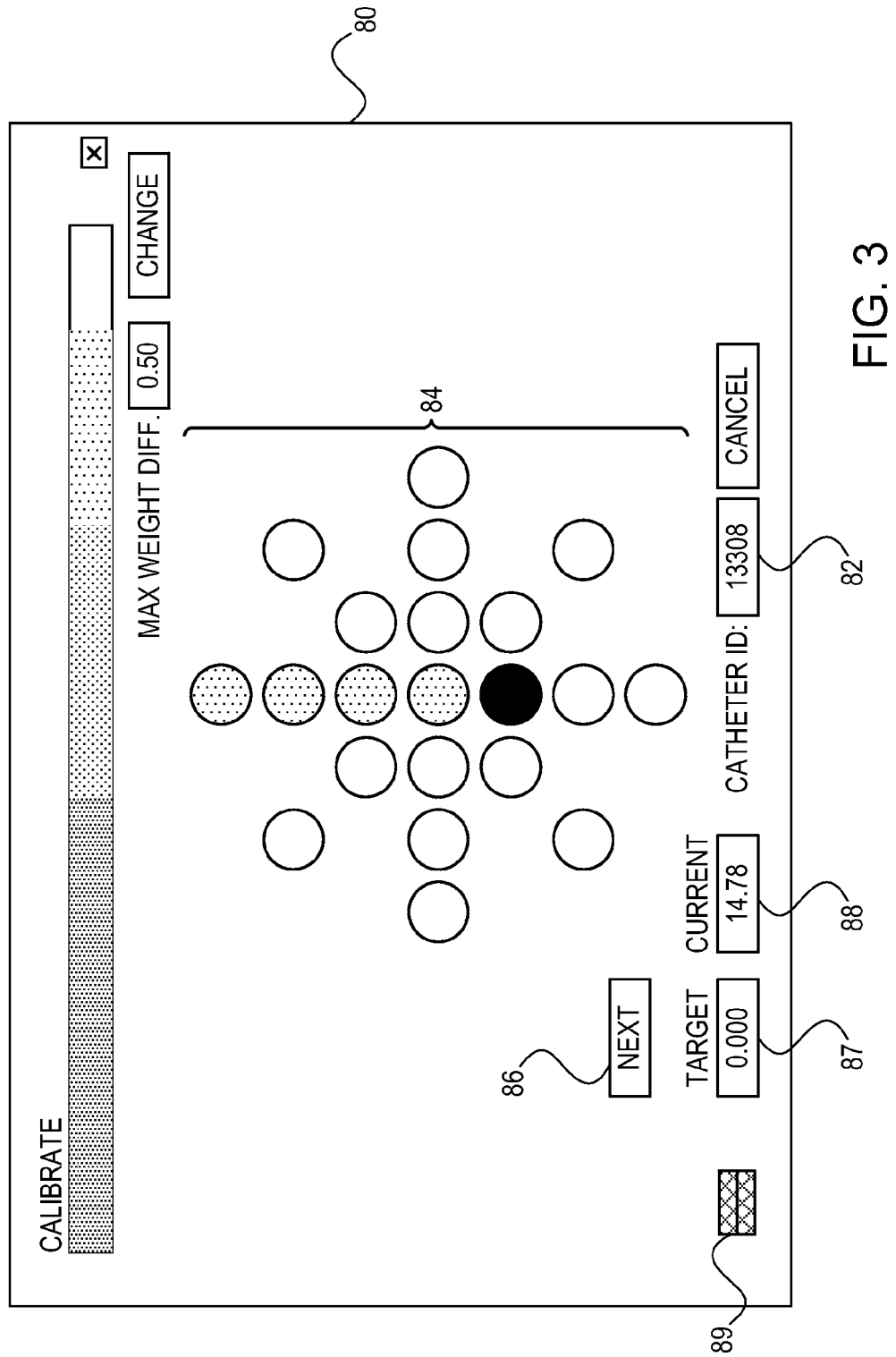
FIG. 3 is a schematic pictorial representation of a graphical user interface of a calibration system for a pressure-sensitive catheter, in accordance with an embodiment of the present invention.

FIG. 3 is a schematic representation of a graphical user interface (GUI) 80 operative to manage calibration of catheter 42, in accordance with an embodiment of the present invention. In this embodiment, display 54 presents GUI 80 to the operator. The operator enters the identity (e.g., a serial number) of the catheter being calibrated into a text box 82 using input device 50. GUI 80 presents a map 84 comprising a diagrammatical representation of insertion holes 38. Each of the insertion holes on the map is color coded to indicate its status during the calibration procedure. For example, in this embodiment, the insertion hole currently being used by the calibration procedure is black, the insertion holes previously used are gray, and the insertion holes not yet used are white. Returning to step 70 in FIG. 2, if additional calibration points are desired, the user presses a "Next" button 86 to identify the next insertion hole to be used in the calibration.

GUI 80 may comprise additional fields or features, such as text boxes 87 and 88 for displaying the target and actual pressure exerted on the catheter, respectively. A bar 89 on the left-hand side of the screen indicates the actual pressure. The GUI shown in FIG. 3 is chosen purely by way of example, and any other suitable GUI can also be used.

Figure 4:
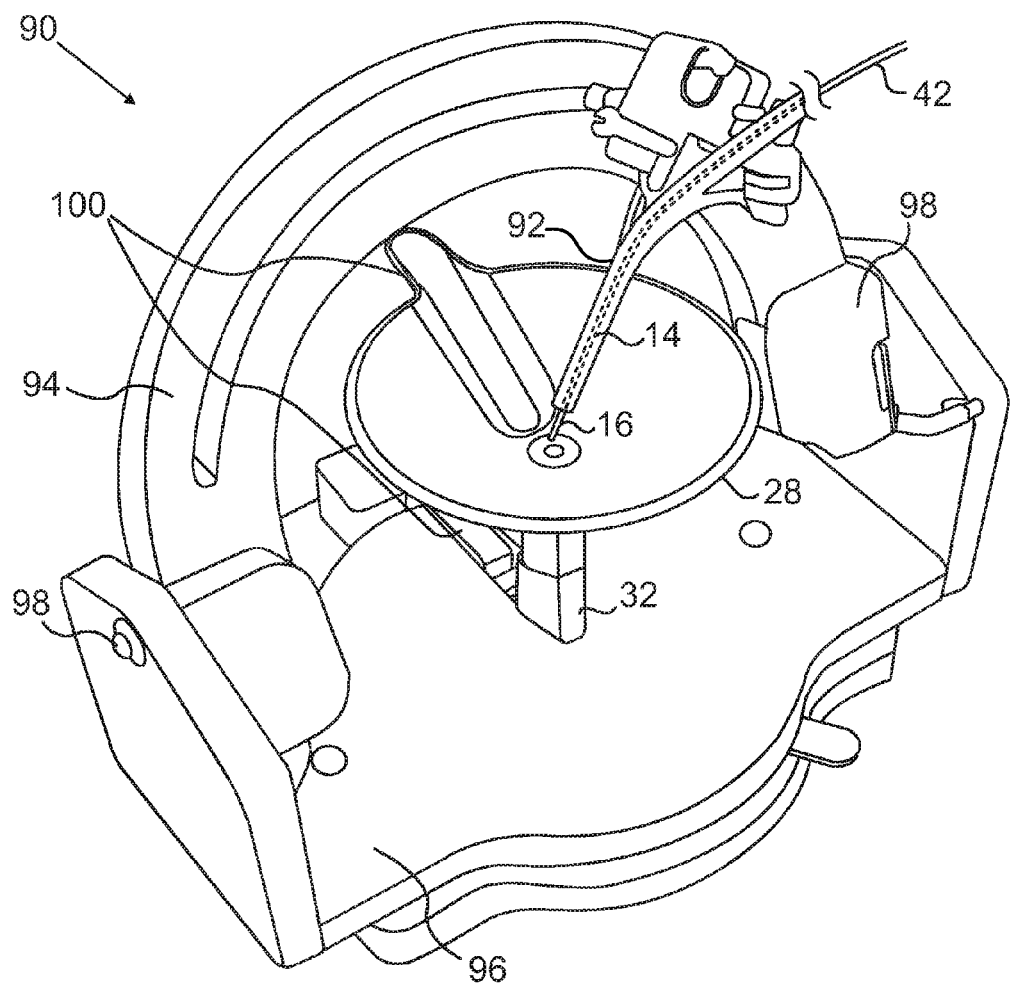
FIG. 4 is schematic pictorial illustration of a calibration system for a pressure-sensitive catheter, in accordance with an alternative embodiment of the present invention.

FIG. 4 is schematic pictorial illustration of a calibration system 90 for catheter 42, in accordance with an alternative embodiment of the present invention. In system 90, a receptacle 92 holds distal end 14, leaving distal tip 16 exposed at joint 18. The proximal end of receptacle 92 is coupled to a track 94. Track 94 is arch-shaped and is coupled to a stand 96 via joints 98. Joints 98 enable track 94 to be rotated in the stand. Positioning receptacle 92 along track 94 and rotating the track enables distal tip 16 to press against cup 28 at a variety of engagement angles. To deflect distal tip (i.e., since track 90 has motion limited to rotation, and the path of receptacle 92 is limited to the track), a lift 100 raises cup 28 and load cell 32, pressing the cup against distal tip 16. A load cell (not shown in the figure) is coupled to the lift and measures the pressure exerted on the catheter tip by the cup. When using the calibration setup of FIG. 4, calibration unit 52 operates similarly to its operation in the setup of FIG. 1 above.

Figure 5:
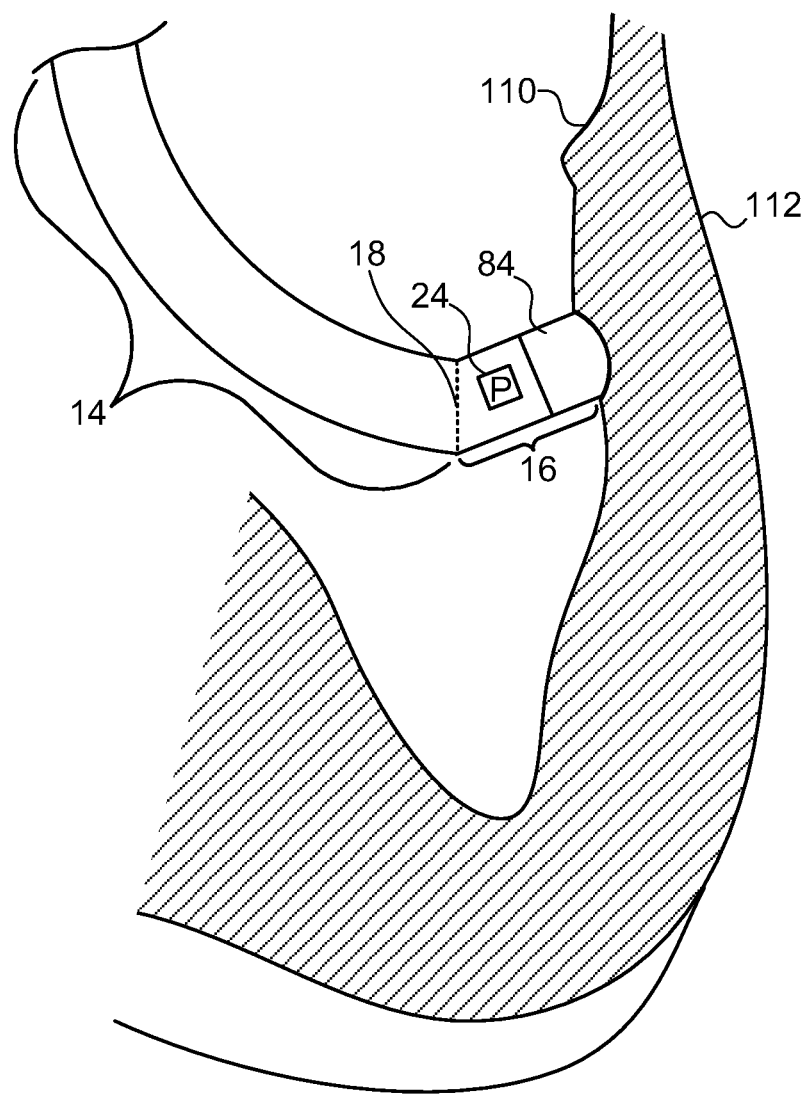
FIG. 5 is a schematic detail view showing the distal tip of a pressure-sensitive catheter in contact with endocardial tissue, in accordance with an embodiment of the present invention.

FIG. 5 is a schematic detail view showing distal tip 16 in contact with an endocardial tissue 110 of a heart 112, in accordance with an embodiment of the present invention. In the present example, tip 16 comprises an electrode 114. In some electrophysiological diagnostic and therapeutic procedures, such as intracardiac electrical mapping, it is important to maintain the proper level of force between electrode 114 and tissue 110. As a medical professional (not shown) presses distal tip 16 against endocardial tissue 110, the catheter bends at joint 18. Sufficient force is needed in order to ensure good electrode contact between the distal tip and the tissue. Poor electrical contact can result in inaccurate readings. On the other hand, excessive force can deform the tissue and thus distort the map.

When tip 16 presses against tissue 110, sensor 24 produces measurements that are indicative of the deflection of tip 16 with respect to distal end 14. The medical imaging system (e.g., mapping system—not shown) translates these measurements into accurate pressure readings using the calibration coefficients stored in memory 44 of the probe. Thus, calibration of the invasive probe using embodiments of the present invention ensures that the medical professional can accurately control the force exerted by the probe on the tissue.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

What is claimed is:

1. A method for calibration, comprising:
    exerting a measurable force on a probe having a distal tip, the measurable force being directed at an engagement angle relative to a reference base angle, so as to cause deflection of the distal tip relative to a distal end of the probe;
    determining the engagement angle;
    determining the exerted force;
    receiving from the probe a position measurement indicative of the deflection between the distal tip and the distal end of the probe;
    determining a force vector from the exerted force at the determined engagement angle; and
    computing one or more calibration coefficients for calibrating the deflection measurement of the probe by mapping the position measurement indicative of the deflection between the distal tip and the distal end against the force vector.

2. The method of claim 1 wherein exerting a force comprises pressing the probe into a force measuring device.

3. The method of claim 2 wherein determining the force comprises receiving from the force measuring device a force measurement indicative of a mechanical force exerted by the distal tip being pressed against the force measuring device.

4. The method of claim 2, wherein pressing the probe into a force measuring device comprises holding the probe in a fixture, the fixture having a receptacle coupled to a track, so as to position the receptacle at one of multiple engagement angles relative to the force measuring device, and raising the fixture in order for the distal tip to press against the force measuring device.

5. The method of claim 4, wherein the fixture comprises a cone-shaped cup.

6. The method of claim 4, wherein the force measuring device comprises a load cell.

7. The method of claim 1 wherein determining the engagement angle comprises inserting the probe into a fixture having of a plurality of insertion holes at predefined angles.

8. The method of claim 7 wherein the insertion holes are labeled with the respective engagement angles, the method further comprises manually inputting the engagement angle manually into a calibration unit.

9. The method of claim 7 wherein the insertion holes are operatively associated with proximity sensors that automatically detect the insertion hole into which the probe is inserted, the method further comprises automatically receiving signals from the proximity sensors and determining which insertion hole is being used based on the signals.

10. The method of claim 1 further comprising immersing the distal end of the probe in a temperature controlled liquid.

11. The method of claim 1 further comprising storing the calibration coefficients in a memory coupled to the probe.

12. The method of claim 11, wherein the memory comprises an $E^2$PROM.

* * * * *